(12) United States Patent
Franke et al.

(10) Patent No.: US 11,801,345 B2
(45) Date of Patent: Oct. 31, 2023

(54) INJECTOR DEVICE

(71) Applicant: SANOFI, Paris (FR)

(72) Inventors: Beate Franke, Frankfurt am Main (DE); Matthias Rau, Rüsselsheim (DE); Tim Gläβer, Rüsselsheim (DE)

(73) Assignee: Sanofi, Paris (FR)

( * ) Notice: Subject to any disclaimer, the term of this patent is extended or adjusted under 35 U.S.C. 154(b) by 495 days.

(21) Appl. No.: 16/768,152

(22) PCT Filed: Nov. 30, 2018

(86) PCT No.: PCT/EP2018/083179
§ 371 (c)(1),
(2) Date: May 29, 2020

(87) PCT Pub. No.: WO2019/106162
PCT Pub. Date: Jun. 6, 2019

(65) Prior Publication Data
US 2020/0368436 A1   Nov. 26, 2020

(30) Foreign Application Priority Data

Dec. 1, 2017   (EP) ..................... 17306674

(51) Int. Cl.
*A61M 5/20*   (2006.01)
*A61M 5/24*   (2006.01)
*A61M 5/32*   (2006.01)

(52) U.S. Cl.
CPC ........ *A61M 5/2033* (2013.01); *A61M 5/2466* (2013.01); *A61M 5/3257* (2013.01); *A61M 2005/2474* (2013.01)

(58) Field of Classification Search
CPC .............. A61M 5/2033; A61M 5/2466; A61M 5/3257; A61M 2005/2474; A61M 5/288;
(Continued)

(56) References Cited

U.S. PATENT DOCUMENTS

| 5,024,616 A | 6/1991 | Ogle, II |
| 5,250,037 A | 10/1993 | Bitdinger |

(Continued)

FOREIGN PATENT DOCUMENTS

| CN | 102905743 | 1/2013 |
| CN | 105939742 | 9/2016 |

(Continued)

OTHER PUBLICATIONS

PCT International Preliminary Report in International Appln. No. PCT/EP2018/083179, dated Jun. 2, 2020, 9 pages.
(Continued)

*Primary Examiner* — Bhisma Mehta
*Assistant Examiner* — Nidah Hussain
(74) *Attorney, Agent, or Firm* — Fish & Richardson P.C.

(57) ABSTRACT

An injector device includes a housing having a slot with a locking portion and a needle unit that has a needle and a slot engagement portion that extends through the slot in the housing to an external side of the housing. The needle unit is movably mounted in the housing such that movement of the needle unit relative to the housing is restricted by the slot. The injector device also includes a cartridge that is mounted in the housing, the cartridge having a reservoir for medicament. Prior to use of the injector device, the reservoir is sealed from the needle. The slot in the housing is arranged such that the needle unit can be rotated to move the slot engagement portion out of the locking portion such that the needle unit can be moved into engagement with the cartridge to place the needle in fluid communication with the reservoir.

22 Claims, 7 Drawing Sheets

(58) Field of Classification Search
CPC ...... A61M 5/285; A61M 5/344; A61M 5/345; A61M 5/346; A61M 5/347; A61M 5/348; A61M 5/3272; A61M 5/2455; A61M 5/3293; A61M 5/2429; A61M 2005/2488; A61M 2005/208; A61M 5/3202; A61M 5/326; A61M 5/20; A61M 2005/2013; A61M 2005/206; A61M 2005/3267
USPC ........................................................ 604/506
See application file for complete search history.

(56) References Cited

U.S. PATENT DOCUMENTS

| | | | |
|---|---|---|---|
| 5,616,128 | A | 4/1997 | Meyer |
| 2002/0177819 | A1* | 11/2002 | Barker ................ A61M 5/3234 604/232 |
| 2011/0125100 | A1 | 5/2011 | Schwirtz et al. |
| 2014/0243741 | A1* | 8/2014 | Kaufmann ............ A61M 5/326 604/88 |
| 2015/0273161 | A1* | 10/2015 | Bengtsson .......... A61M 5/3286 604/198 |

FOREIGN PATENT DOCUMENTS

| | | |
|---|---|---|
| CN | 106456892 | 2/2017 |
| CN | 106456899 | 2/2017 |
| GB | 836278 | 6/1960 |
| JP | H02-243163 | 9/1990 |
| JP | 2013-544166 | 12/2013 |
| JP | 2016-526460 | 9/2016 |
| WO | WO 2011/117284 | 9/2011 |
| WO | WO 2012/072563 | 6/2012 |
| WO | WO 2015/004049 | 1/2015 |
| WO | WO 2015/117854 | 8/2015 |
| WO | WO 2015/150578 | 10/2015 |
| WO | WO 2015/185664 | 12/2015 |
| WO | WO 2016/202829 | 12/2016 |
| WO | WO 2017/089284 | 6/2017 |
| WO | WO 2017/089289 | 6/2017 |

OTHER PUBLICATIONS

PCT International Search Report and Written Opinion in International Appln. No. PCT/EP2018/083179, dated Jan. 7, 2019, 13 pages.

* cited by examiner

INJECTOR DEVICE

CROSS REFERENCE TO RELATED APPLICATIONS

The present application is the national stage entry of International Patent Application No. PCT/EP2018/083179, filed on Nov. 30, 2018, and claims priority to Application No. EP 17306674.7, filed on Dec. 1, 2017, the disclosures of which are incorporated herein by reference.

TECHNICAL FIELD

The present disclosure relates to an injector device for a medicament.

BACKGROUND

Cartridge injection devices, for example cartridge auto-injectors, typically have a sealed cartridge that contains a medicament and a needle that is initially separated from the cartridge. Before use of the injector device the cartridge and needle are combined so that the needle pierces the cartridge. A plunger can then be moved into the cartridge to dispense medicament through the needle for injection to a user.

SUMMARY

It is an object of the present disclosure to provide an advantageous injector device having a cartridge with a reservoir for medicament that is initially sealed from a needle, and a mechanism for moving the needle into fluid communication with the reservoir in the cartridge prior to use.

According to the present disclosure, there is provided an injector device comprising:
  a housing comprising a slot having a locking portion,
  a needle unit comprising a needle, an inner part to which the needle is mounted, a slot engagement portion, and an outer part disposed externally of the housing, wherein the slot engagement portion extends from the inner part through the slot in the housing to the outer part of the housing, the needle unit being movably mounted in the housing such that movement of the needle unit relative to the housing is restricted by the slot, and
  a cartridge mounted in the housing, the cartridge having a reservoir for medicament, wherein prior to use of the injector device the reservoir is sealed from the needle, and wherein the slot in the housing is arranged such that rotation of the outer part of the needle unit moves the slot engagement portion out of the locking portion such that the needle unit can be moved into engagement with the cartridge to place the needle in fluid communication with the reservoir.

The slot in the housing may further comprise a movement portion that permits the needle unit to move towards the cartridge after the needle unit has been rotated.

In some embodiments, the injector device has a longitudinal axis, and the cartridge and the needle may be aligned with the longitudinal axis such that the needle is axially spaced from the cartridge. In these examples, the movement portion of the slot may extend in an axial direction.

The injector device may further comprise a spring arranged to urge the needle unit towards the cartridge. The spring may be arranged to move the needle unit into engagement with the cartridge after rotation of the needle unit.

The locking portion of the slot may be angled with respect to the movement portion, and the spring may be arranged to urge the needle unit into a locked position at an end of the locking portion remote from the movement portion. In examples, the slot may be arranged such that needle unit must be moved away from the cartridge before the needle unit can be rotated. In this way, the locked position is stable and the user must overcome at least some of the force of the spring to rotate the needle unit to move the slot engagement portion into the movement portion of the slot.

The slot in the housing may extend to an end of the housing, and the slot may comprise a retaining member arranged to prevent the needle unit detaching from the housing.

In some examples, the injector device further comprises a needle sleeve slidably mounted to the housing to protrude from the distal end of the housing.

The needle sleeve may comprise a slot, and the slot engagement portion of the needle unit may engage the slot of the needle sleeve.

The slot of the needle sleeve may comprise a movement portion corresponding to the movement portion of the slot of the housing to permit movement of the needle unit independently of the needle sleeve after rotation of the needle unit.

The needle sleeve may be slidably mounted in the housing and a restricting member may prevent from the needle sleeve from rotating relative to the housing. The restricting member may engage a groove to prevent rotation of the needle sleeve relative to the housing. In one example, needle sleeve comprises the restricting member and the housing comprises the groove. In another example, the housing comprises the restricting member and the needle sleeve comprises the groove.

In examples, the injector device further comprises a plunger and a spring arranged to urge the plunger into the reservoir to dispense medicament. A catch may be arranged to hold the plunger in a pre-loaded state prior to use of the device. The needle sleeve may be configured to release the catch when the needle sleeve moves into the housing.

The outer part of the needle unit may comprise one or more discrete sections.

The cartridge may comprise a medicament disposed in the reservoir.

According to another aspect of the present disclosure, there is also provided a method of using an injector device, the injector device comprising a housing, a needle unit having a needle and an outer part disposed externally of the housing, and a cartridge having a reservoir for medicament, wherein prior to use of the injector device the reservoir is sealed from the needle,
  the method comprising:
  rotating the outer part of the needle unit relative to the housing,
    and moving the needle unit into engagement with the cartridge such that the needle is placed in fluid communication with the reservoir.

These and other aspects of the disclosure will be apparent from and elucidated with reference to the embodiments described hereinafter.

BRIEF DESCRIPTION OF THE FIGURES

Embodiments will now be described, by way of example only, with reference to the accompanying drawings, in which.

DETAILED DESCRIPTION

Figure 1A:
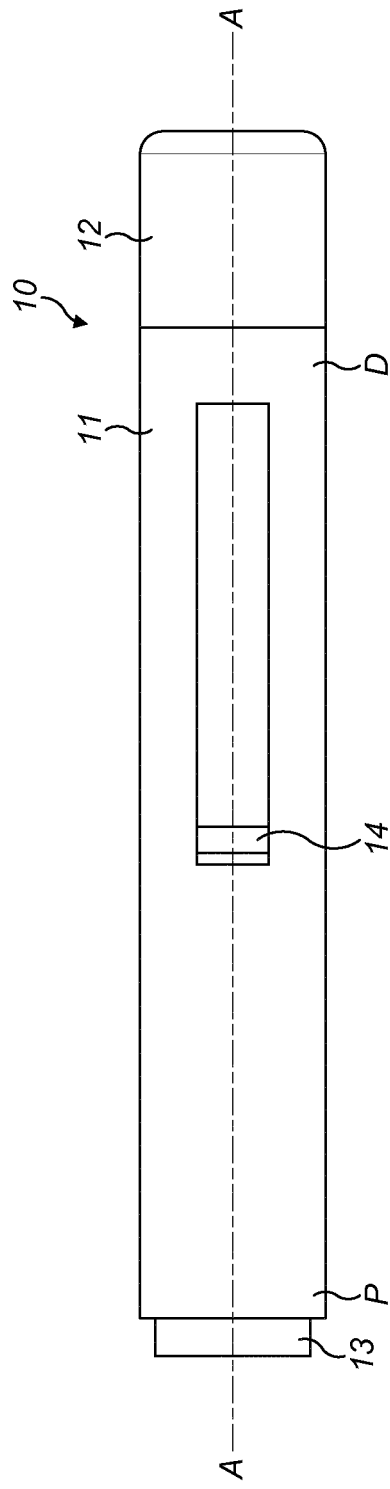
FIG. 1A is a schematic side view of an injector device and a removable cap.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 17 and 29 Gauge.

The delivery devices described herein can also include one or more automated functions. For example, one or more of combining the needle and cartridge, needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of combining the needle and cartridge, needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
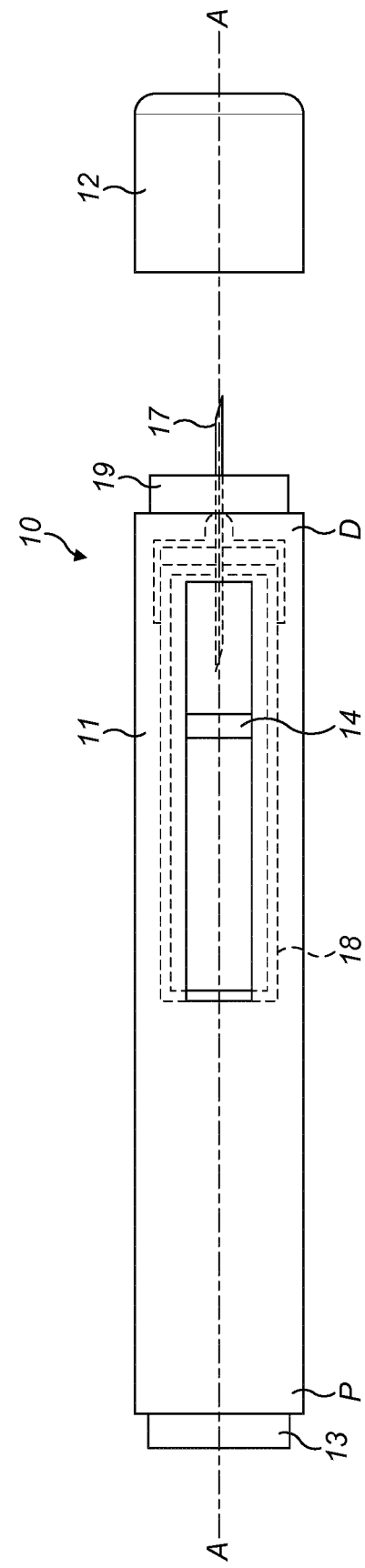
FIG. 1B is a schematic side view of the injector device of FIG. 1A, with the cap removed from the housing.

According to some embodiments of the present disclosure, an exemplary drug delivery device 10 is shown in FIGS. 1A and 1B. Device 10, as described above, is configured to inject a medicament into a patient's body. Device 10 includes a housing 11 which typically contains a cartridge that defines a reservoir containing the medicament to be injected, and the components required to facilitate one or more steps of the delivery process.

The device 10 can also include a cap 12 that can be detachably mounted to the housing 11. Typically, a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated", whereby needle 17 moves relative to housing 11. Such insertion can be triggered by movement of sleeve 19 or by another form of activation, such as, for example, a button 13. As shown in FIGS. 1A and 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location to a more distal location within the reservoir of the cartridge 18 in order to force a medicament from the cartridge 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the cartridge 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the cartridge 18 within housing 11 is moved in a proximal direction relative to housing 11. This proximal movement can be achieved by using a retraction spring (not shown), located in distal region D. A compressed retraction spring, when activated, can supply sufficient force to the cartridge 18 to move it in a proximal direction. Following sufficient retraction, any relative movement between needle 17 and housing 11 can be locked with a locking mechanism. In addition, button 13 or other components of device 10 can be locked as required.

Figure 2:
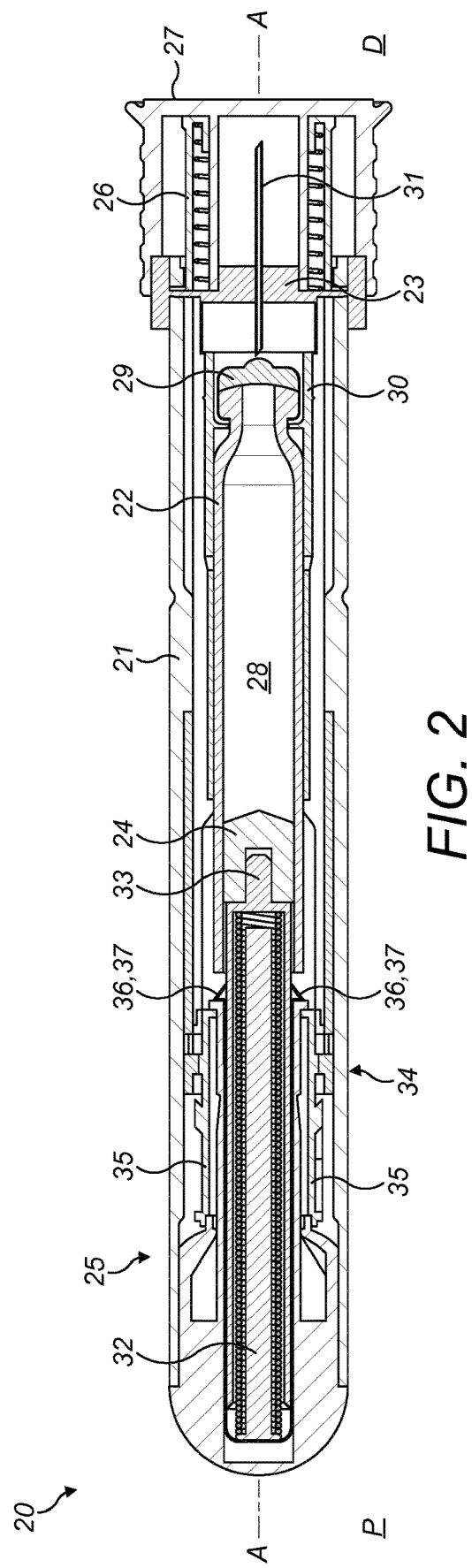
FIG. 2 is a cross-sectional view of an injector device.

FIG. 2 illustrates an example injector device 20 having a housing 21, a cartridge 22, and a needle unit 23. The injector device 20 further includes a piston 24, a piston drive mechanism 25, and a needle sleeve 26, which is initially covered by a cap 27, as illustrated.

The cartridge 22 defines a reservoir 28 that contains a medicament and is mounted within the housing 21. A distal end D of the cartridge 22 is sealed by an end cap 29. A cartridge mounting portion 30 of the housing 21 supports the cartridge 22.

As shown in FIG. 2, in an initial condition the needle 31 of the needle unit 23 is spaced from the end cap 29 at the distal end of the cartridge 22. Before or during use of the injector device 20 the needle unit 23 is moved into engagement with the distal end of the cartridge 22 such that the needle 31 pierces the end cap 30 of the cartridge 22. In this way, medicament can be expelled from the reservoir 28 via the needle 31, as explained further hereinafter.

In the initial condition, illustrated in FIG. 2, the piston 24 is disposed at a proximal end of the reservoir 28 in the cartridge 22, and the piston drive mechanism 25 is disposed in the proximal end of the housing 21. The piston drive mechanism 25 comprises a spring 32, a plunger 33, and a catch 34. The spring 32 is arranged to urge the plunger 33 against the piston 24 and into the cartridge 22 to expel medicament from the reservoir 28 during use. In the initial position before use, as illustrated, the spring 32 is held in a compressed state by a catch 34. Specifically, the catch 34 holds the plunger 33, which holds the spring 32 in a compressed state such that no force is applied to the piston 24.

As explained further hereinafter, the injector device 20 is actuated by an actuator, in this example a needle sleeve 26 that is slidably movable within the housing 21 and protrudes from the distal end of the housing 21. In this way, during use, the needle sleeve 26 is placed against the user's skin and the injector device 20 is pushed towards the user's skin while holding the housing 21, this moves the needle sleeve 26 in a proximal direction, into the housing 21.

The needle sleeve 26 acts to release the catch 34 once the needle sleeve 26 has moved into the housing 21 in a proximal direction. Once the catch 34 is released, the spring 32 urges the plunger 33 against the piston 24 and into the reservoir 28.

As illustrated in FIG. 2, the catch 34 may include a tubular element 35 that surrounds the plunger 33 and spring 32. The tubular element 35 includes protrusions 36 that engage recesses 37 in the plunger 33, such that in the position illustrated in FIG. 2 the plunger 33 is prevented from moving in a distal direction by the protrusions 36 and the recesses 37.

As the needle sleeve 26 is moved proximally into the housing 21, an end of the needle sleeve 26 engages the tubular element 35, causing the tubular element 35 to rotate about the axis A of the injector device 20. This rotation causes the protrusions 36 to disengage from the recesses 37, thereby releasing the plunger 33, which then moves under the force of the spring 32 into the reservoir 28.

In one example, the end of the needle sleeve 26 that engages the tubular element 35 may comprise a chamfer (i.e. angled edge) that engages a protrusion on the tubular element 35 to cause the rotation. In other examples, the tubular element 35 may comprise a chamfer (i.e. angled edge) that is engaged by a protrusion on the needle sleeve 26 to cause the rotation.

In other examples, the catch 34 may comprise arms that include the protrusions that engage the plunger 33. In this case, the needle sleeve 26 might deflect the arms by lifting them to disengage the protrusions from the recesses, thereby releasing the plunger 33.

Before or during use, the needle unit 23 is combined with the cartridge 22 before the catch 34 is released. As explained below, rotating the needle unit 23 causes the needle unit 23 to move axially within the housing 21 and engage the cartridge 22, and a subsequent movement of the needle sleeve 26 in a proximal direction releases the catch 34 so that plunger 33 begins delivery of the medicament via the needle 31.

Figure 3A:
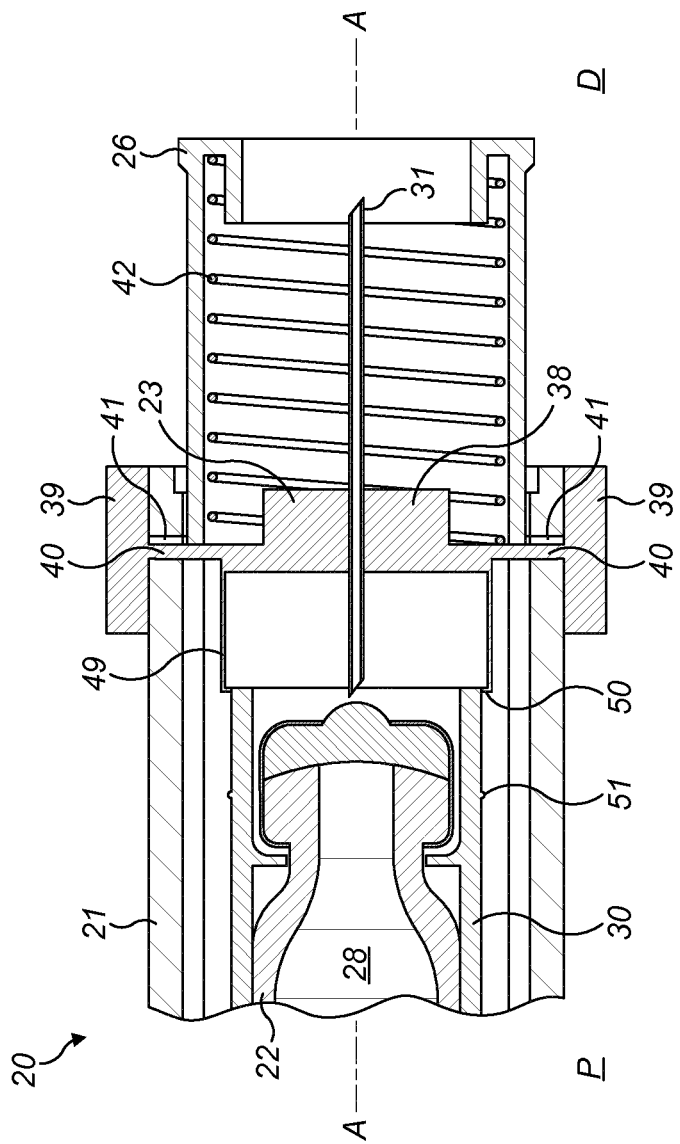
FIG. 3A is a cross-sectional view of the needle-end of the injector device of FIG. 2 in an initial position.

FIG. 3A illustrates an initial condition of the injector device 20, before use. As illustrated, the housing 21 is tubular at the distal end, and the needle unit 23 is mounted to the housing 21. In particular, the needle unit 21 comprises an inner part 38 to which the needle 31 is mounted, an outer part 39 that is disposed on an outer circumferential surface of the housing 21, and a slot engagement portion 40 that extends through a slot 41 in the housing 21 to join the inner part 38 to the outer part 39.

The housing 21 may include one slot 41 or a plurality of slots, for example two, three, or four slots. The needle unit 23 includes the same number of slot engagement portions 40, so there is one slot engagement portion 40 for each slot 41. The outer part 39 of the needle unit 23 may be discrete parts that are joined to the ends of the slot engagement portions 40. In this way, the outer part 39 does not necessarily extend fully circumferentially about the housing 21, but may be one or more buttons that can be actuated by the user.

The needle unit 23 is mounted in the housing 21 such that the needle unit 23 can rotate about the longitudinal axis A of the injector device 20, and can move in an axial direction within the housing 21. The cartridge 22 is mounted to the housing 21 such that the cartridge 22 is fixed within the housing 21. In particular, as illustrated, the housing 21 includes a cartridge mounting portion 30 that surrounds at least a part of the cartridge 22 to hold it in position. In the illustrated example, the cartridge mounting portion 30 surrounds a distal end of the cartridge 22.

Furthermore, as illustrated, the needle sleeve 26 is slidably mounted to the distal end of the housing 21. The needle sleeve 26 is mounted such that it can slide in an axial direction, but cannot rotate. For example, the needle sleeve 26 comprises a restricting member that engages a groove in the internal surface of the housing 21 to permit axial sliding but not rotation. Alternatively, the needle sleeve 26 comprises a groove, and the housing 21 comprises a restricting member that engages the groove to permit axial sliding but not rotation. In addition, the needle sleeve 26 and/or the housing 21 includes a protrusion that prevents the needle sleeve 26 from detaching from the housing 21 (i.e. moving in a distal direction from the position shown in FIG. 3A).

The needle sleeve 26 also includes a slot (not shown in FIG. 3A) through which the slot engagement portion 40 of the needle unit 23 extends. The slot in the needle sleeve 26 corresponds to the slot 41 in the housing 21.

As illustrated, a spring 42 is disposed between the needle unit 23 and the needle sleeve 26, and urges them apart, so that the needle sleeve 26 is urged in a distal direction, away from the housing 21, and the needle unit 23 is urged in a proximal direction, towards the cartridge 22.

Figure 4C:
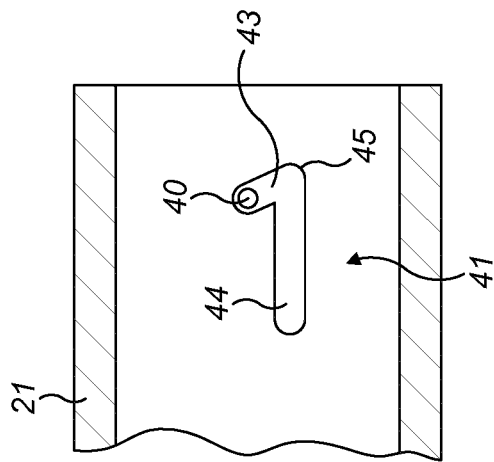
FIGS. 4A to 4C are schematic views of different slots in the housing of the injector device; and, FIGS. 5A to 5D illustrate operation of the injector device.
Figure 4B:
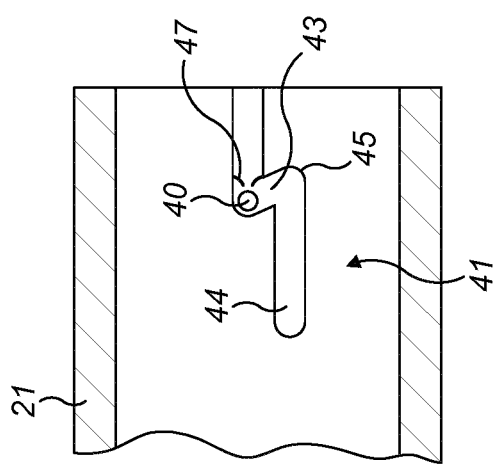
Figure 4A:
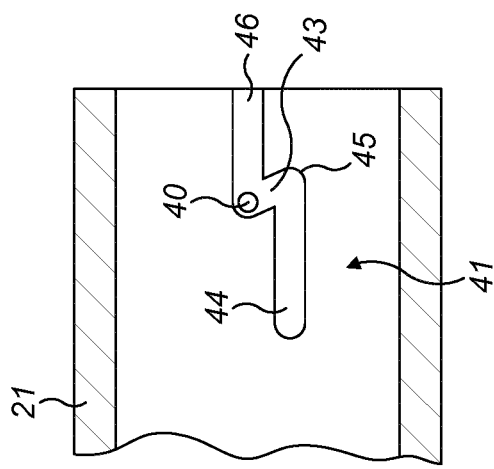

Various examples of the slot 41 in the housing 21 are illustrated in FIGS. 4A to 4C. In these examples the slot 41 comprises a locking portion 43 and a movement portion 44. As illustrated, when the slot engagement portion 40 of the needle unit (23, see FIG. 3A) is located in the locking portion 43 of the slot 41, with the spring (42, see FIG. 3A) urging the needle unit (23, see FIG. 3A) in a proximal direction, the slot engagement portion 40 is urged into an end of the locking portion 43 that is remote to the movement portion 44. Therefore, the position of the needle unit (23, see FIG. 3A) relative to the housing 21 is 'locked'.

Referring to FIG. 3A and FIGS. 4A to 4C, rotation of the needle unit 23 relative to the housing 21 moves the slot engagement portion 40 of the needle unit 23 out of the locking portion 43 and into the movement portion 44, allowing the spring 42 to move the needle unit 23 in a proximal direction relative to the housing 21.

As shown, the movement portion 44 of the slot 41 extends in a direction parallel to the axis A of injector device 20, between the distal and proximal ends. The locking portion 43 is angled with respect to the movement portion 44. The angle between the locking portion 43 and the movement portion 44 is such that a vertex 45 is defined at a distal end of the both the locking portion 43 and the movement portion 44. In this way, the needle unit 23 must be moved a small distance in a distal direction and rotated in order to move the slot engagement portion 40 of the needle unit 23 from the locking portion 43 to the movement portion 44, i.e. to 'unlock' the needle unit 23.

In the example of FIG. 4A, the slot 41 also includes a portion 46 that extends to a distal end of the housing 21. In the example of FIG. 4B, retaining members 47 are disposed in the slot 41 to prevent the slot engagement portion 40 of the needle unit 23 from entering the portion 46 of the slot 41 that extends to the distal end of the housing 21. The retaining members 47 thereby prevent detachment of the needle unit 23 from the housing 21. Alternatively, as illustrated in FIG. 4C, the slot 41 may not comprise a portion that extends to a distal end of the housing 21. In this example, the slot 41 comprises only a locking portion 43 and a movement portion 44.

The slot (48, see FIGS. 3B and 3C) in the needle sleeve 26 corresponds to the slot 41 in the housing 21. Specifically, the slots 41, 48 both include a locking portion 43 and a movement portion 44, which are aligned with each other. In this way, rotation and axial movement of the needle unit 23 relative to the housing 21 is independent of the needle sleeve 26, which can therefore remain in the same position while the needle unit 23 is moved into engagement with the cartridge 22.

In the initial state, illustrated in FIG. 3A, the spring 42 is under compression and the components are held in this state due to the slot 41 in the housing 23 and the slot 48 in the needle sleeve 26. In particular, in this initial state the spring 42 is urging the slot engagement portion 40 of the needle unit 23 into the locked position within the slot 41 in the housing 21, and is also urging the slot engagement portion 40 into a locked position within the slot 48 in the needle sleeve 26.

The needle unit 23 can be rotated by the user by gripping the outer part 39 of the needle unit 23 and rotating the needle unit 23 relative to the housing 21. This moves the slot engagement portion 40 of the needle unit 23 out of the locking portion 43 and into the movement portion 44 of the slot 41. The rotation of the needle unit 23 also moves the slot engagement portion 40 into the movement portion of the slot 48 in the needle sleeve 26.

Figure 3B:
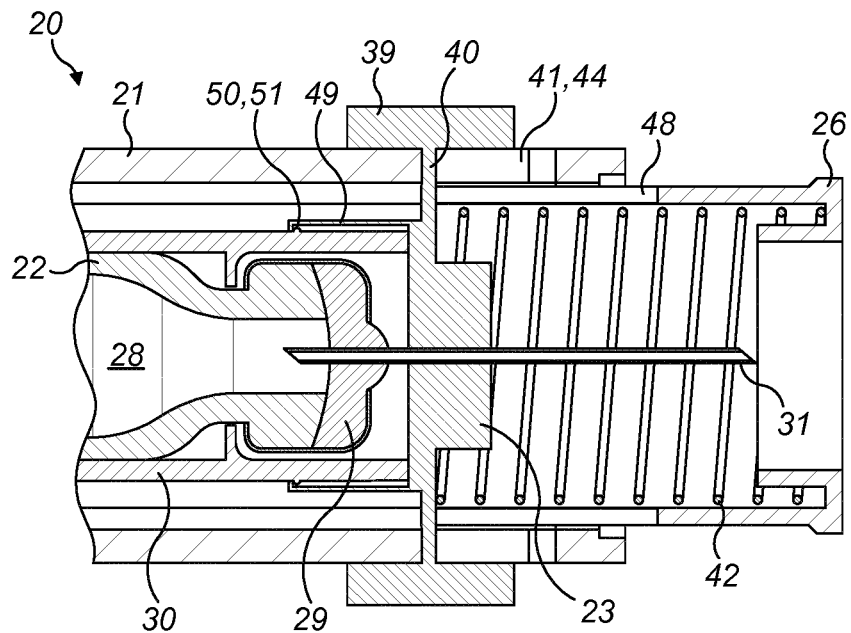
FIG. 3B is a cross-sectional view of the needle-end of the injector device of FIG. 2 after the needle unit and cartridge have been combined.

This allows the spring 42 to move the needle unit 23 in a proximal direction. FIG. 3B illustrates the positions of the needle unit 23 and needle sleeve 26 after the needle unit 23 has been rotated. As shown, the needle unit 23 has moved proximally and engaged the cartridge 22. In particular, the needle 31 has pierced the end cap 29 of the cartridge 22 so that the needle 31 is in fluid communication with the reservoir 28 and medicament can be delivered from the cartridge 22 via the needle 31.

As illustrated in FIG. 3B, the needle sleeve 26 is in the same position as the initial position of FIG. 3A because the slot engagement portion 40 has moved along the slot 48 in the needle sleeve 26 at the same time as moving along the slot 41 in the housing 21. Therefore, after rotation of the needle unit 23, the needle unit 23 moves into engagement with the cartridge 22, and the needle sleeve 26 remains in the same location (i.e. protruding from the distal end of the housing 21).

In the above-described examples, the slot 48 in the needle sleeve 26 also prevents movement of the needle sleeve 26 in a proximal direction (to release the plunger 33, see FIG. 2) until the needle unit 23 has been rotated. That is, the locking position between the slot engagement portion 40 and the slot 48 in the needle sleeve 26 prevents movement of the needle sleeve 26 into the housing 21 until the needle unit 23 has been rotated to move the slot engagement portion 40 into the movement portion of the slot 48 in the needle sleeve 26. Therefore, the catch (34, see FIG. 2) and plunger (33, see FIG. 2) cannot be released until the needle unit 23 has been rotated to engage the needle unit 23 and the cartridge 22.

Figure 3C:
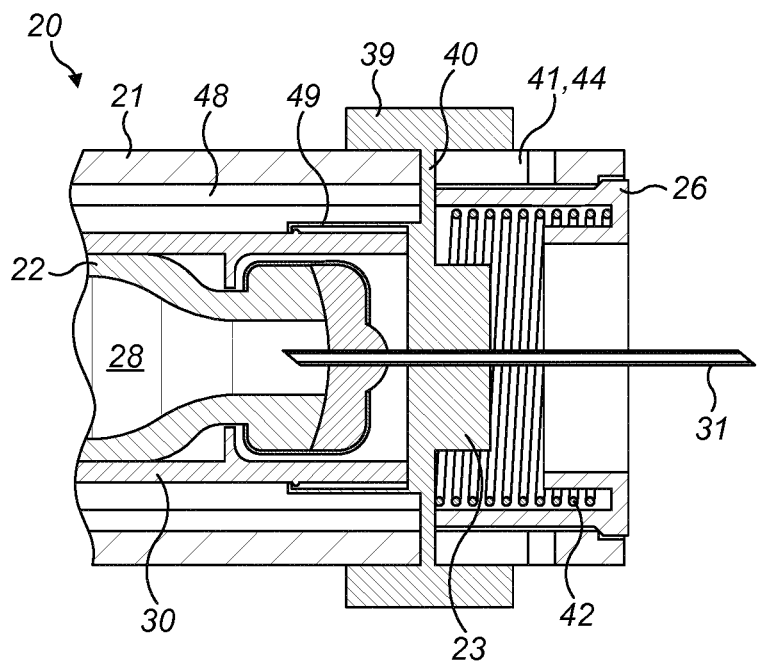
FIG. 3C is a cross-sectional view of the needle-end of the injector device of FIG. 2 during injection.

As illustrated in FIGS. 3A to 3C, the needle unit 23 further comprises locking members 49 that engage the cartridge 22 when the needle unit 23 moves into engagement with the cartridge 22. In particular, the needle unit 23 has snap-lock parts 49 that engage the cartridge mounting portion 30 of the housing 21. Therefore, once the needle unit 23 has reached the position illustrated in FIG. 3B, the needle unit 23 is 'locked' onto the cartridge mounting portion 30, and is locked relative to the cartridge 22.

The snap-lock parts 49 include a pair of flexible arms, each with a catch 50 at the end. The catches 50 are adapted to latch onto a part 51 of the cartridge mounting portion 30 of the housing 21 in the vicinity of the cartridge 22. Alternatively, the catches 50 may be adapted to latch into a recess located on the housing 21 in the vicinity of the cartridge 22, for example in the cartridge mounting portion 30. Alternatively, the catches 50 may be adapted to latch onto a catch or recess on the cartridge 22 itself.

Thereafter, the injector device 20 is used by pressing the distal end of the needle sleeve 26 against a users skin, which causes the needle sleeve 26 to move into the housing 21 in a proximal direction, exposing the needle 31. As described with reference to FIG. 2, such axial proximal movement of the needle sleeve 26 also releases the catch 34, beginning delivery of the medicament by the plunger 33.

Operation of the injector device 20 is illustrated with reference to FIGS. 5A to 5D.

Figure 5A:
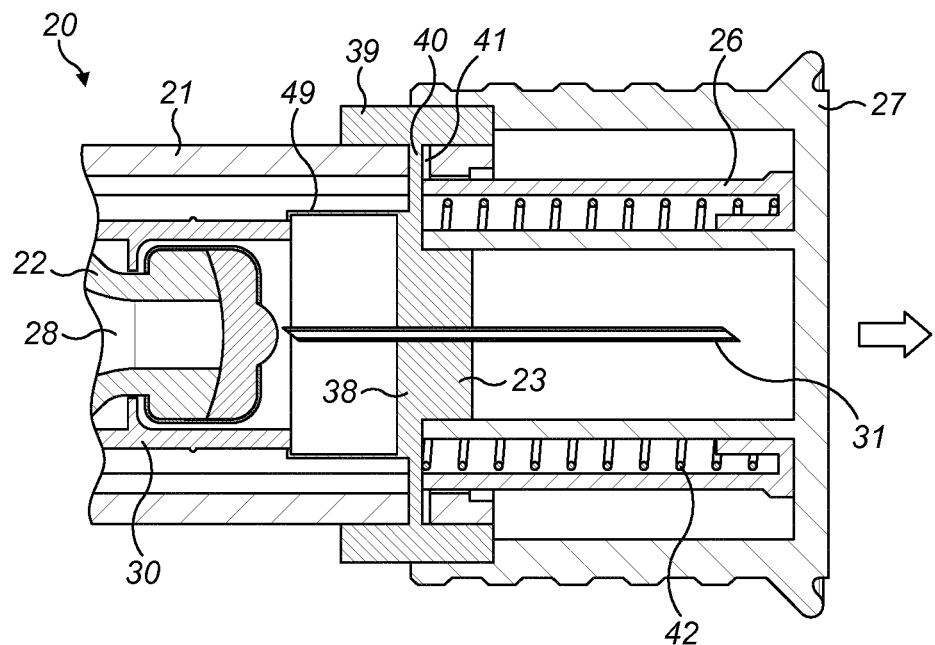

FIG. 5A shows the initial state of the injector device 20, with a cap 27 covering the needle sleeve 26 and the needle 31 being spaced from the cartridge 22. As shown, the locking members 49 of the inner part 38 of the needle unit 23 are in contact with a part of the cartridge mounting portion 30 of the housing 21 and will act to guide the needle unit 23 when it is moved towards the cartridge 22.

In this state, the slot engagement portion 40 of the needle unit 23 is disposed in the locking portion (43, see FIGS. 4A to 4C) of the slot 40 in the housing 21, and in the locking portion of the slot (48, see FIGS. 3B and 3C) in the needle sleeve 26, such that the position of the needle unit 23 is locked relative to the housing 21 and the cartridge 22. In addition, the slot (48, see FIGS. 3B and 3C) in the needle sleeve 26 prevents the needle sleeve 26 from moving in a proximal direction relative to the housing 21.

Figure 5B:
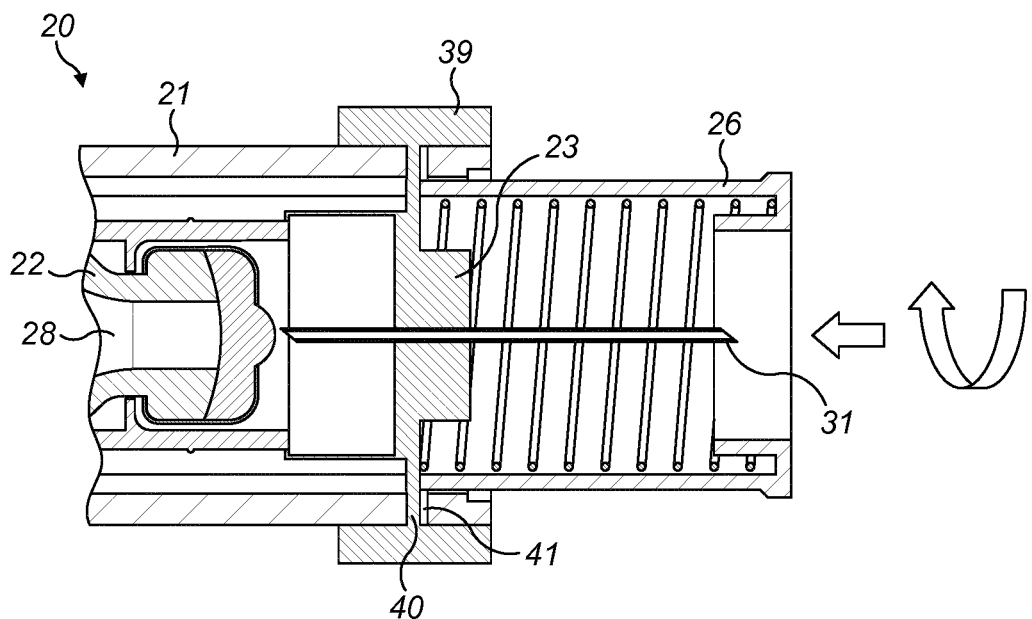
Figure 5C:
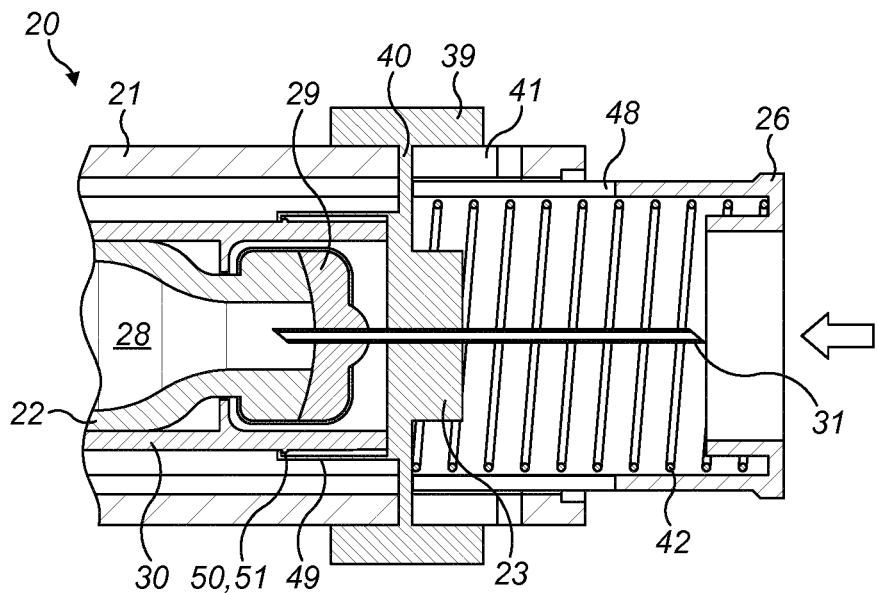

Once the cap 27 is removed, the needle unit 23 can be rotated using the outer part 39 of the needle unit 23. FIG. 5B shows the injector device 20 before the needle unit 23 has been rotated, and FIG. 5C shows the injector device 20 after the needle unit 23 has been rotated. The rotation of the needle unit 23 moves the slot engagement portion 40 of the needle unit 23 into the movement portion 44 of the slot 41 in the housing 21 and the movement portion of the slot 48 in the needle sleeve 26. Therefore, the needle unit 23 is free to move in an axial direction relative to the housing 21 and needle sleeve 26, and the spring 42 pushes the needle unit 23 into engagement with the cartridge 22, as shown in FIG. 5C.

In the state of FIG. 5C, the needle 31 has pierced the end cap 29 of the cartridge 22 and is in fluid communication with the reservoir 28. The locking members 49 have locked the needle unit 23 onto the cartridge mounting portion 30 of the housing 21. The injector device 20 is now able to dispense medicament through the needle 31.

Figure 5D:
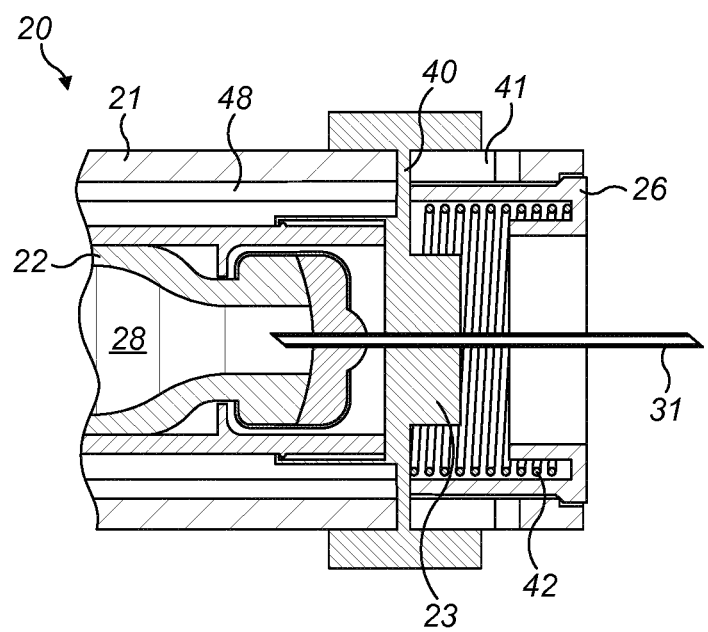

To initiate the injection process, as illustrated in FIG. 5D, the needle sleeve 26 is pressed against the user's skin so that the needle sleeve 26 is moved into the housing 21 in a proximal direction, thereby exposing the needle 31, which pierces the user's skin. As explained previously, movement of the needle sleeve 26 in the proximal direction also disengages the catch (34, see FIG. 2), releasing the plunger (33, see FIG. 2) so that the spring (32, see FIG. 2) drives the plunger (33, see FIG. 2) into the cartridge 22 to dispense medicament via the needle 31. As the needle sleeve 26 moves in a proximal direction the slot 48 in the needle sleeve 26 allows the needle sleeve 26 to move independently of the needle unit 23, which remains in its engaged position on the cartridge 22.

Once the injection process is completed and the injector device 20 is removed from the user's skin, the spring 42 urges the needle sleeve 26 back into the extended position (FIG. 5C), so that the needle 31 is covered again.

In various examples, the injector device 20 does not include a needle sleeve 26. In these examples, the user rotates the needle unit 23 and moves it axially to engage the cartridge 22, and then the injection process (i.e. releasing the catch 34, see FIG. 2) can be carried out by a different actuator, for example a button or lever that the user presses once the needle 31 has been inserted into the skin. In these examples, the spring 42 may also be omitted. In some examples, an alternative spring may be provided to act between the housing 21 and the needle unit 23, to urge the slot engagement portion 40 of the needle unit 23 into the locking portion 43 of the slot 41 in the housing 21 prior to use, and to urge the needle unit 23 into engagement with the cartridge 22 after rotation of the needle unit 21. In other examples, no spring is provided, and the user manually moves the needle unit 23 into engagement with the cartridge 22 by rotating the needle unit 23 and then sliding the needle unit 23 onto the cartridge 22.

Moreover, it will be appreciated that the plunger 33 may not be driven by a spring 32, as illustrated in FIG. 2. For example, the plunger 33 may be manually operated, so that the user pushes the plunger 33 into the cartridge 22 after rotation of the needle unit 23. Alternatively, a motor or linear drive mechanism may be provided to move the plunger 33 into the cartridge 22 after rotation of the needle unit 23.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide. Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten. An examples of an oligonucleotide is, for example: mipomersen sodium (Kynamro®), a cholesterol-reducing antisense therapeutic for the treatment of familial hypercholesterolemia. Examples of DPP4 inhibitors are Vildagliptin, Sitagliptin, Denagliptin, Saxagliptin, Berberine. Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synviscd®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

The invention claimed is:

1. An injector device comprising:
a housing comprising a slot having a locking portion;
a needle unit comprising a needle, an inner part to which the needle is mounted, a slot engagement portion, and an outer part disposed externally of the housing, wherein the slot engagement portion extends from the inner part through the slot in the housing to the outer part, the needle unit being movably mounted in the housing such that movement of the needle unit relative to the housing is restricted by the slot; and
a cartridge mounted in the housing, the cartridge having a reservoir for medicament,
wherein prior to use of the injector device the reservoir is sealed from the needle, and wherein the slot in the housing is arranged such that rotation of the outer part of the needle unit moves the slot engagement portion out of the locking portion such that the needle unit can be moved into engagement with the cartridge to place the needle in fluid communication with the reservoir.

2. The injector device of claim 1, wherein the slot in the housing further comprises a movement portion that permits the needle unit to move towards the cartridge after the needle unit has been rotated.

3. The injector device of claim 2, further comprising a spring arranged to urge the needle unit towards the cartridge.

4. The injector device of claim 3, wherein the locking portion of the slot is angled with respect to the movement portion.

5. The injector device of claim 4, wherein the spring is arranged to urge the needle unit into a locked position at an end of the locking portion remote from the movement portion.

6. The injector device of claim 2, wherein the injector device further comprises a needle sleeve slidably mounted to the housing to protrude from the distal end of the housing.

7. The injector device of claim 6, wherein the slot is a first slot, and wherein the needle sleeve comprises a second slot.

8. The injector device of claim 7, wherein the movement portion is a first movement portion, and wherein the second slot of the needle sleeve comprises a second movement portion corresponding to the first movement portion of the first slot of the housing to permit movement of the needle unit independently of the needle sleeve after rotation of the needle unit.

9. The injector device of claim 7, wherein the slot engagement portion of the needle unit engages the first slot of the housing and the second slot of the needle sleeve.

10. The injector device of claim 6, wherein the needle sleeve is slidably mounted in the housing.

11. The injector device of claim 10, wherein a restricting member prevents the needle sleeve from rotating relative to the housing.

12. The injector device of claim 6, further comprising:
a plunger; and
a spring arranged to urge the plunger into the reservoir to dispense medicament.

13. The injector device of claim 12, wherein a catch is arranged to hold the plunger in a pre-loaded state prior to use of the injector device.

14. The injector device of claim 13, wherein the needle sleeve is configured to release the catch when the needle sleeve moves into the housing.

15. The injector device of claim 1, wherein the slot is arranged such that needle unit must be moved away from the cartridge before the needle unit can be rotated.

16. The injector device of claim 1, wherein the slot in the housing extends to an end of the housing.

17. The injector device of claim 16, wherein the slot comprises a retaining member arranged to prevent the needle unit from detaching from the housing.

18. The injector device of claim 1, wherein the outer part of the needle unit comprises one or more discrete sections.

19. The injector device of claim 1, wherein the cartridge comprises a medicament disposed in the reservoir.

20. The injector device of claim 1, wherein the needle unit is rotatable by gripping the outer part of the needle unit and rotating the needle unit relative to the housing.

21. The injector device of claim 1, wherein the outer part is disposed on an outer circumferential surface of the housing.

22. A method of using an injector device, the injector device comprising: a housing comprising a slot having a locking portion, a needle unit having a needle, an inner part to which the needle is mounted, a slot engagement portion, and an outer part disposed externally of the housing, wherein the slot engagement portion extends from the inner part through the slot in the housing to the outer part, the needle unit being movably mounted in the housing such that movement of the needle unit relative to the housing is restricted by the slot, and a cartridge mounted in the housing and having a reservoir for medicament, wherein prior to use of the injector device the reservoir is sealed from the needle, and wherein the slot in the housing is arranged such that rotation of the outer part of the needle unit moves the slot engagmenet portion out of the locking portion such that the needle unit can be moved into engagement with the cartridge to place the needle in fluid communication with the reservoir, wherein the method comprises:

rotating the outer part of the needle unit relative to the housing; and moving the needle unit into engagement with the cartridge such that the needle is placed in fluid communication with the reservoir.

\* \* \* \* \*

UNITED STATES PATENT AND TRADEMARK OFFICE
CERTIFICATE OF CORRECTION

| | |
|---|---|
| PATENT NO. | : 11,801,345 B2 |
| APPLICATION NO. | : 16/768152 |
| DATED | : October 31, 2023 |
| INVENTOR(S) | : Beate Franke, Matthias Rau and Tim Glasser |

It is certified that error appears in the above-identified patent and that said Letters Patent is hereby corrected as shown below:

In the Claims

In Column 15, Line 18, Claim 22, delete "engagmenet" and insert -- engagement --

In Column 15, Line 19, Claim 22, delete "cartidge" and insert -- cartridge --

Signed and Sealed this
Twenty-ninth Day of October, 2024

Katherine Kelly Vidal
*Director of the United States Patent and Trademark Office*